US011266524B2

(12) United States Patent
Rosen et al.

(10) Patent No.: US 11,266,524 B2
(45) Date of Patent: Mar. 8, 2022

(54) MEDICAL METHODS AND SYSTEMS FOR SKIN TREATMENT

(71) Applicant: R2 Technologies, Inc., San Ramon, CA (US)

(72) Inventors: Jesse Rosen, Albany, CA (US); Kevin Springer, Livermore, CA (US); Kristine Tatsutani, Redwood City, CA (US); Michael O'Neil, Dublin, CA (US); Benjamin Sun, Mountain View, CA (US); Erik Stauber, Albany, CA (US)

(73) Assignee: R2 TECHNOLOGIES, INC., San Ramon, CA (US)

(*) Notice: Subject to any disclaimer, the term of this patent is extended or adjusted under 35 U.S.C. 154(b) by 1115 days.

(21) Appl. No.: 15/612,740

(22) Filed: Jun. 2, 2017

(65) Prior Publication Data
US 2017/0348143 A1 Dec. 7, 2017

Related U.S. Application Data

(60) Provisional application No. 62/430,782, filed on Dec. 6, 2016, provisional application No. 62/345,303, filed on Jun. 3, 2016.

(51) Int. Cl.
*A61F 7/00* (2006.01)
*A61H 23/00* (2006.01)
*A61H 23/02* (2006.01)

(52) U.S. Cl.
CPC ............ *A61F 7/0085* (2013.01); *A61F 7/007* (2013.01); *A61H 23/008* (2013.01);
(Continued)

(58) Field of Classification Search
CPC .............. A61F 7/0085; A61F 7/007; A61F 2007/0087; A61F 2007/0052;
(Continued)

(56) References Cited

U.S. PATENT DOCUMENTS 3,664,344 A 5/1972 Bryne
4,206,609 A 6/1980 Durenec et al.
(Continued)

FOREIGN PATENT DOCUMENTS

CN 104490372 A 4/2015
DE 9217897 11/1993
(Continued)

OTHER PUBLICATIONS

Andrews, "Cryosurgery for Common Skin Conditions", American Family Physician, vol. 69 Issue 10, May 15, 2004, pp. 2365-2372.
(Continued)

*Primary Examiner* — Kaitlyn E Smith
*Assistant Examiner* — Yasamin Ekrami
(74) *Attorney, Agent, or Firm* — Kilpatrick Townsend & Stockton LLP

(57) ABSTRACT

The present invention generally relates to improved medical devices, systems, and methods, with exemplary embodiments providing improved cooling treatment probes and cooling treatment methods and systems. In some embodiments, freezing of the skin may be desirable to effect the hypopigmentation of the skin of the patient. Generally, embodiments may limit supercooling of the skin of the patient during a cooling treatment. Additionally, embodiments may limit adverse side effects such as hyperpigmentation. It has been found that the freezing behavior (frequency and time to freeze) can be modified by adjusting the thermal parameters of the cooling applicator. Accordingly, in some aspects of the invention, a method of treating the skin (Continued)

may be provided where the thermal parameters of the cooling applicator are adjusted during treatment.

43 Claims, 7 Drawing Sheets

(52) U.S. Cl.
CPC ............... A61F 2007/0052 (2013.01); A61F 2007/0063 (2013.01); A61F 2007/0075 (2013.01); A61F 2007/0086 (2013.01); A61F 2007/0087 (2013.01); A61F 2007/0093 (2013.01); A61F 2007/0096 (2013.01); A61H 23/0236 (2013.01); A61H 23/0245 (2013.01); A61H 23/0263 (2013.01); A61H 2201/0153 (2013.01); A61H 2201/0214 (2013.01); A61H 2201/0257 (2013.01); A61H 2201/0285 (2013.01); A61H 2201/5028 (2013.01); A61H 2201/5061 (2013.01); A61H 2230/505 (2013.01)

(58) Field of Classification Search
CPC ...... A61F 2007/0063; A61F 2007/0075; A61F 2007/0093; A61F 2007/0295; A61F 2007/0296; A61H 2201/0285; A61H 2201/0214; A61H 2201/0153; A61H 23/0245; A61H 2230/505; A61H 2201/5061; A61H 2201/5028; A61H 2201/0257
See application file for complete search history.

(56) References Cited

U.S. PATENT DOCUMENTS

| | | | |
|---|---|---|---|
| 5,374,284 A | 12/1994 | Guibert et al. | |
| 5,596,875 A | 1/1997 | Berry et al. | |
| 5,759,182 A | 6/1998 | Varney et al. | |
| 5,848,981 A | 12/1998 | Herbranson | |
| 5,901,707 A | 5/1999 | Goncalves et al. | |
| 6,017,337 A | 1/2000 | Pira | |
| 6,430,956 B1 | 8/2002 | Haas et al. | |
| 6,503,246 B1 | 1/2003 | Har-shai et al. | |
| 6,629,417 B2 | 10/2003 | Haas et al. | |
| 6,981,970 B2 | 1/2006 | Kami et al. | |
| 7,367,341 B2 | 5/2008 | Anderson et al. | |
| 7,630,774 B2 | 12/2009 | Britva et al. | |
| 7,751,452 B2 | 7/2010 | Vogler | |
| 7,850,683 B2 | 12/2010 | Elkins et al. | |
| 8,150,532 B2 | 4/2012 | Britva et al. | |
| 8,435,194 B2 | 5/2013 | Dverin et al. | |
| 8,579,835 B2 | 11/2013 | Britva et al. | |
| 8,950,406 B2 | 2/2015 | Karni et al. | |
| 9,522,031 B2 | 12/2016 | Manstein et al. | |
| 2003/0100936 A1 | 5/2003 | Altshuler et al. | |
| 2004/0030332 A1* | 2/2004 | Knowlton | A61N 1/30 |
| | | | 606/41 |
| 2004/0167592 A1 | 8/2004 | Grove et al. | |
| 2005/0222565 A1 | 10/2005 | Manstein et al. | |
| 2006/0058238 A1 | 3/2006 | Laurent-Applegate et al. | |
| 2006/0189976 A1 | 8/2006 | Kami et al. | |
| 2006/0282067 A1 | 12/2006 | Koop et al. | |
| 2007/0088386 A1 | 4/2007 | Babaev et al. | |
| 2007/0129714 A1 | 6/2007 | Elkins et al. | |
| 2007/0135876 A1 | 6/2007 | Weber et al. | |
| 2007/0185527 A1 | 8/2007 | Babaev | |
| 2008/0039747 A1 | 2/2008 | Baerwalde et al. | |
| 2008/0077201 A1 | 3/2008 | Levinson et al. | |
| 2008/0119839 A1 | 5/2008 | Vancelette et al. | |
| 2008/0183164 A1 | 7/2008 | Elkins et al. | |
| 2008/0183167 A1 | 7/2008 | Britva et al. | |
| 2008/0287943 A1 | 11/2008 | Weber et al. | |
| 2009/0012585 A1 | 1/2009 | Karni et al. | |
| 2009/0018623 A1 | 1/2009 | Levinson et al. | |
| 2009/0171424 A1 | 7/2009 | Britva et al. | |
| 2009/0281537 A1 | 11/2009 | Britva et al. | |
| 2009/0299355 A1* | 12/2009 | Bencini | A61B 18/02 |
| | | | 606/21 |
| 2010/0036295 A1 | 2/2010 | Altshuler et al. | |
| 2010/0114007 A1 | 5/2010 | Fischer et al. | |
| 2011/0313411 A1 | 12/2011 | Anderson et al. | |
| 2012/0041525 A1 | 2/2012 | Kami et al. | |
| 2012/0071794 A1 | 3/2012 | Karni et al. | |
| 2012/0123319 A1 | 5/2012 | Britva et al. | |
| 2012/0330194 A1 | 12/2012 | Britva et al. | |
| 2014/0007895 A1 | 1/2014 | Britva et al. | |
| 2014/0135662 A1 | 5/2014 | Britva et al. | |
| 2014/0260331 A1* | 9/2014 | Lofy | F25B 21/02 |
| | | | 62/3.3 |
| 2014/0303696 A1 | 10/2014 | Anderson et al. | |
| 2014/0303697 A1 | 10/2014 | Anderson et al. | |
| 2015/0045857 A1 | 2/2015 | Karni et al. | |
| 2015/0057701 A1* | 2/2015 | Kelleher | A61H 23/0236 |
| | | | 606/204.15 |
| 2015/0080991 A1 | 3/2015 | Karni et al. | |
| 2015/0182375 A1 | 7/2015 | Binversie et al. | |
| 2015/0216719 A1 | 8/2015 | Debenedictis et al. | |
| 2015/0216720 A1* | 8/2015 | DeBenedictis | A61B 18/02 |
| | | | 601/15 |
| 2015/0223975 A1* | 8/2015 | Anderson | A61B 18/02 |
| | | | 607/104 |
| 2016/0157915 A1 | 6/2016 | Anderson et al. | |
| 2016/0317346 A1* | 11/2016 | Kovach | A61B 5/721 |
| 2016/0354559 A1* | 12/2016 | Gavini | A61M 15/0085 |
| 2017/0065323 A1 | 3/2017 | Rosen et al. | |
| 2017/0325992 A1* | 11/2017 | DeBenedictis | A61K 9/0014 |

FOREIGN PATENT DOCUMENTS

| | | |
|---|---|---|
| EP | 1797847 | 6/2007 |
| EP | 2201917 | 6/2010 |
| EP | 2272455 | 1/2011 |
| GB | 2286660 | 8/1995 |
| JP | 04133822 | 5/1992 |
| JP | 10052475 | 2/1998 |
| JP | 2005237908 | 9/2005 |
| KR | 200431404 | 11/2006 |
| KR | 100802155 | 2/2008 |
| RU | 2074680 | 3/1997 |
| WO | 2003/078596 | 9/2003 |
| WO | 2005096979 | 10/2005 |
| WO | 2006066226 | 6/2006 |
| WO | 2006127467 | 11/2006 |
| WO | 2007064718 | 6/2007 |
| WO | 2008055243 | 5/2008 |
| WO | 2008083305 | 7/2008 |
| WO | 2008091983 | 7/2008 |
| WO | 2009146053 | 12/2009 |
| WO | 2010017477 | 2/2010 |
| WO | 2013075006 | 5/2013 |
| WO | 2013075016 | 5/2013 |
| WO | 2017041022 | 3/2017 |
| WO | 2017196548 | 11/2017 |

OTHER PUBLICATIONS

Gage et al., "Critical Temperature for Skin Necrosis in Experimental Cryosurgery", Cryobiology 19, 1982, 273-282.
Gage et al., "Sensitivity of Pigmented Mucosa and Skin to Freezing Injury", Cryobilogy 16, 1979, 348-361.
Har-Shai et al., "Effect of skin surface temperature on skin pigmentation during contact and intralesional cryosurgery of hypertrophic scars and Kleoids", Journal of the European Academy of Dermatology and Venereology, vol. 21, Issue 2, Feb. 2007, pp. 191-198.
Thai et al., "Cryosurgery of Benign Skin Lesions", Australasian Journal of Dermatology 40, 1999, 175-186.
Yeh, "Cryosurgical Treatment of Melanin-Pigmented Gingiva", Mackay Memorial Hospital, Jun. 1998, 1-4.
Zachariassen et al., "Ice Nucleation and Antinucleation in Nature", Cryobiology, vol. 41 Issue 4, Dec. 2000, pp. 257-279.

(56) References Cited

OTHER PUBLICATIONS

EP17807609.7 , "Extended European Search Report", dated Jan. 3, 2020, 7 pages.

* cited by examiner

MEDICAL METHODS AND SYSTEMS FOR SKIN TREATMENT

CROSS REFERENCE TO RELATED APPLICATIONS

The present application claims the benefit of U.S. Provisional Patent Appln. No. 62/345,303 filed Jun. 3, 2016, and U.S. Provisional Patent Appln. No. 62/430,782 filed Dec. 6, 2016; the full disclosures of which are incorporated herein by reference in their entirety for all purposes.

BACKGROUND

Embodiments of the present invention generally relate to methods, devices, and systems for reducing a pigmentation of a skin of a patient. More specifically, embodiments generally relate to methods, devices, and systems to increase the consistency of skin treatment by reliably freezing (water phase transition) the skin during treatment and limiting adverse side effects from the skin freezing.

Controlled freezing of biological tissue, such as skin tissue, can produce various effects. Certain tissue freezing procedures and devices, such as conventional cryoprobes, can cause severe freezing of tissue and generate cellular damage. It has been observed that moderate degrees of freezing can produce particular effects, such as affecting the expression of skin pigmentation (e.g., hypopigmentation).

There is a demand for cosmetic products that can lighten the appearance of skin or otherwise controllably affect skin pigmentation. For example, it may be desirable to lighten the overall complexion or color of a region of skin to alter the general appearance for cosmetic reasons. Also, lightening of particular hyperpigmented regions of skin, such as large freckles, 'café au lait' spots, melasma, or dark circles under the eyes that may result from excessive local amounts of pigment in the skin, may also be desirable for cosmetic reasons. Hyperpigmentation can result from a variety of factors such as UV exposure, aging, stress, trauma, inflammation, etc. Such factors can lead to an excess production of melanin, or melanogenesis, in the skin by melanocytes, which can lead to formation of hyperpigmented areas. Such hyperpigmented areas are typically associated with excess melanin within the epidermis; however, they can also result from excess melanin deposited within the dermis.

Hypopigmentation of skin tissue has been observed as a side effect in response to temporary cooling or freezing of the tissue, such as may occur during cryosurgery procedures. Loss of pigmentation following skin cooling or freezing may result from decreased melanin production, decreased melanosome production, destruction of melanocytes, or inhibited transfer of melanosome into the keratinocytes in the lower region of the epidermal layer. The resultant hypopigmentation may be long-lasting or permanent. However, it has also been observed that some of these freezing procedures can generate regions of hyperpigmentation (or skin darkening) of skin tissue. The level of increase or decrease in pigmentation may be dependent upon certain aspects of the cooling or freezing conditions, including the temperature of the cooling treatment, and the length of time the tissue is maintained in a frozen state.

While some hypopigmentation treatments, devices, and systems have been previously developed, further improvements may be desired. Toward this end, it may be desirable to improve the consistency of skin freezing. Such improvements may be desirable to improve overall hypopigmentation consistency. For example, with some cooling treatments, the skin may sometimes freeze toward the beginning of the cooling treatment, or may sometimes cool to a temperature below the freezing point (e.g., 0 to $-5°$ C.) for a period and then freeze some variable time thereafter. With some cooling treatments, the skin may become supercooled (cooled to a temperature below the freezing point) and may not freeze at all during the cooling treatment. Such variability in the skin freezing (i.e., the formation of water ice in the skin) may result in less than optimal treatment. Additionally, prolonging treatment and/or applying colder temperatures is not necessarily a solution as it may result in adverse side effects such as hyperpigmentation.

In light of the above, it may be desirable to improve the consistency or repeatability of hypopigmentation treatments, in particular hypopigmentation treatments provided via skin freezing. At least some embodiments of the present invention may provide additional control over the occurrence of freezing and may limit supercooling of the skin during a cooling treatment. Additionally, at least some embodiments may provide skin treatment while limiting adverse side effects, such as hyperpigmentation.

SUMMARY

The present invention generally relates to improved medical devices, systems, and methods, with exemplary embodiments providing improved cooling treatment probes and cooling treatment methods and systems. In some embodiments, freezing of the skin may be desirable to effect the hypopigmentation of the skin of the patient. Generally, embodiments may limit supercooling of the skin of the patient during a cooling treatment. Additionally, embodiments may limit adverse side effects such as hyperpigmentation.

In some aspects of the present invention, a method of altering pigmentation in a skin of a patient may be provided. The method may include pre-cooling a cooling applicator of a treatment device to a pre-treatment temperature prior to contact of the cooling applicator with a skin surface of the patient. The pre-treatment temperature may be colder than a treatment temperature. After the cooling applicator is positioned onto the skin surface and while the applicator is maintained against the skin, the cooling applicator may be driven toward the pre-treatment temperature for a first duration of time to pre-condition the skin to freeze. After the first duration of time and while the cooling applicator is positioned and maintained against the skin surface, the cooling applicator may be adjusted toward the treatment temperature for a second duration of time. The treatment temperature may be configured to freeze at least a portion of the skin tissue in contact with the cooling applicator.

In some embodiments, the second duration of time may be longer than the first duration of time. The treatment temperature may be below $0°$ C. The pre-treatment temperature may be in a range from $-10°$ C. to $-20°$ C. The treatment temperature may be in a range from $-2°$ C. to $-10°$ C.

Optionally, the second duration of time may be three to ten times longer in duration than the first duration of time. In certain embodiments, the second duration of time may be less than 5 seconds.

The method may further include adjusting the cooling applicator toward a post-treatment temperature that is higher than the treatment temperature after the second duration of time and while the cooling applicator is positioned and maintained against the skin. The post-treatment temperature may be applied so as to thaw the frozen skin tissue. In some embodiments, a thermoelectric cooler is thermally coupled with the cooling applicator. Adjusting the cooling applicator to the post-treatment temperature may include the step of reversing a current through the thermoelectric cooler. Optionally, the current may be reversed until the cooling applicator reaches the post-treatment temperature. In some embodiments, the post-treatment temperature is above 0° C. The post treatment temperature may be less than 10° C., or less than less than 40° C. The cooling applicator may be maintained in contact with the skin at the post-treatment temperature until the frozen portion of skin thaws.

In still further aspects, a method of treating a skin of a patient may be provided that includes cooling a cooling applicator of a treatment device to a pre-treatment temperature prior to contacting the skin with the cooling applicator of the treatment device. The pre-treatment temperature may be colder than a treatment temperature. The pre-treatment temperature may be configured to pre-condition at least a portion of the skin to freeze. The cooling applicator may then be placed onto the skin and the treatment device may cool the cooling applicator toward the pre-treatment temperature during the first duration of time. After the first duration of time, the cooling applicator may be maintained against the skin for a second duration of time while the treatment device adjusts the cooling applicator toward the treatment temperature. The cooling applicator may be removed from the skin of the patient after treating the skin to the treatment temperature using the cooling applicator of the treatment device. In some embodiments, the second duration of time may be longer than the first duration of time.

In still further aspects, a skin treatment system may include a cooling applicator for contacting a skin of a patient, a cooling arrangement thermally coupled with the cooling applicator; and a controller operably coupled with the cooling arrangement. The controller may be configured to control the cooling arrangement to provide a cooling treatment cycle. The cooling treatment cycle may include pre-cooling of the cooling applicator to a pre-treatment temperature prior to contact with the skin of the patient and cooling of the cooling applicator toward the pre-treatment temperature for a first duration of time after the cooling applicator is placed against the skin of the patient. The cooling treatment cycle may further include, after the first duration of time, adjustment of the temperature of the cooling applicator toward a treatment temperature that is higher than the pre-treatment temperature while the cooling applicator is held against the skin and cooling of the cooling applicator toward the treatment temperature for a second duration of time while the cooling applicator is held against the skin.

In some embodiments, the second duration of time may be longer than the first duration of time. The treatment temperature may be below zero. The pre-treatment temperature may be −10° C. to −20° C. Optionally, the treatment temperature may be −2° C. to −10° C.

The second duration of time may be three to ten times longer in duration than the first duration of time. In some embodiments, the second duration of time may be less than 5 seconds.

The cooling treatment cycle may further include, after the second duration of time and while the cooling applicator is placed against the skin, adjustment of the temperature of the cooling applicator toward a post-treatment temperature that is higher than the treatment temperature.

In some embodiments, the cooling applicator may be a thermoelectric cooler. The controller may adjust the cooling applicator toward the post-treatment temperature by reversing a current through the thermoelectric cooler.

The post-treatment temperature may be above 0° C. The post-treatment temperature may be less than 10° C., or less than 40° C. in certain embodiments.

In some embodiments, the device may further comprise a force sensor coupled with the controller. The force sensor may be configured to measure a force between the cooling applicator and the skin of a patient. The first duration of time or the second duration of time may be variable based on the force measured by the force sensor.

In some embodiments, the device may further include a force sensor coupled with the controller. The force sensor may be configured to measure a force between the cooling applicator and the skin of a patient. The pre-treatment temperature or the treatment temperature may be variable based on the force measured by the force sensor.

Optionally, the device may include a contact sensor coupled with the controller. The contact sensor may be configured to determine contact between the cooling applicator and the skin of the patient. The controller may initiate the cooling treatment cycle based on skin contact as determined by the contact sensor.

In some embodiments, a contact sensor may be coupled with the controller. The contact sensor may be configured to determine contact between the cooling applicator and the skin of the patient. The controller may return the cooling arrangement to the pre-treatment temperature when skin contact is not sensed by the contact sensor.

In still further aspects, a method of reducing melanin in a skin of a patient using a cooling applicator of a treatment device may be provided. The method may include pre-cooling the cooling applicator to a pre-treatment temperature of −10° C. to −20° C. prior to positioning cooling applicator in contact with the skin; cooling the cooling applicator toward the pre-treatment temperature for a first duration of time after the cooling applicator has been positioned onto the skin; after the first duration of time and while the cooling applicator is placed against the skin, adjusting the cooling applicator toward a treatment temperature of −2° C. to −12° C. for a second duration of time that is longer than the first duration of time; and after the second duration of time and while the cooling applicator is placed against the skin, adjusting the cooling applicator toward a post-treatment temperature between 0° C. to 40° C. In some embodiments, the cooling applicator can be adjusted toward a treatment temperature of −2° C. to −10° C. In some embodiments, the cooling applicator can be adjusted toward a post-treatment temperature between 0° C. to 10° C. or between 0° C. to 40° C.

In other aspects, a skin pigmentation treatment system is provided that may include a cooling applicator for contacting a skin of a patient; a thermoelectric cooler thermally coupled with the cooling applicator; and a controller operably coupled with the thermoelectric cooler. The controller may be configured to control a current to the thermoelectric cooler to provide a cooling treatment cycle. The cooling treatment cycle may include application of a current to the thermoelectric cooler to cool the cooling applicator toward a treatment temperature while the cooling applicator is held against the skin for a duration of time; and, after the duration of time, reversing the current to the thermoelectric cooler to adjust a temperature of the cooling applicator toward a post-treatment temperature while the cooling applicator is held against the skin. The post-treatment temperature may be less than 10° C. or less than 40° C.

In still further embodiments, a method of altering pigmentation in a skin of a patient may be provided that includes supercooling the skin of the patient by placing a cooling applicator of a treatment device against a skin surface. After supercooling the skin, the method may include applying vibrations to the skin of the patient to facilitate ice crystal formation in the supercooled skin.

In some embodiments, the skin of the patient may be supercooled for a predetermined amount of time before the application of vibrations.

Optionally, after applying vibrations to the skin of the patient, the method may include maintaining the cooling applicator against the skin surface for a first duration of time. After the first duration of time, and while the cooling applicator is positioned and maintained against the skin, the method may include adjusting the temperature toward a post-treatment temperature to thaw the frozen skin tissue. The post-treatment temperature may be between 0° C. to 10° C. or between 0° C. to 40° C. The first duration of time may be between 10-30 seconds. Optionally, the cooling applicator may be driven toward a treatment temperature during the first duration of time. The treatment temperature may be between −2° C. to −10° C. or between −2° C. to −12° C.

In some embodiments, the treatment temperature or the first duration of time may be variable based on a force between the cooling applicator and the skin of the patient.

In some embodiments, the method may include returning the cooling applicator of the treatment device toward an idle state based on a signal from a contact sensor indicating removal of the cooling applicator from the skin of the patient.

In still further embodiments, a skin treatment system may be provided that includes a cooling applicator for contacting a skin of a patient, a cooling arrangement thermally coupled with the cooling applicator, and a controller operably coupled with the cooling arrangement and a vibrator. The controller may be configured to control the cooling arrangement and the vibrator to provide a cooling treatment. The cooling treatment may include cooling of the cooling applicator to supercool the skin of the patient and application of the vibrator to deliver vibrations into the supercooled skin to facilitate ice formation in the skin.

The controller may be configured to supercool the skin of the patient for a predetermined amount of time before applying vibrations from the vibrator.

The controller may be configured to adjust the cooling applicator to a treatment temperature for a first duration of time after applying vibrations to the skin of the patient.

The controller may be configured to adjust the temperature of the cooling applicator toward a post-treatment temperature to thaw the frozen skin tissue after the first duration of time, and while the cooling applicator is positioned and maintained against the skin.

In some embodiments, the post-treatment temperature may be between 0° C. to 10° C., or between 0° C. to 40° C.

In some embodiments, the first duration of time may be between 10-30 seconds.

Optionally, the treatment temperature may be between −2° C. to −10° C.

The device may further include a force sensor coupled with the controller. The force sensor may be configured to measure a force between the cooling applicator and the skin of the patient. The treatment temperature or the first duration of time may be variable based on a force between the cooling applicator and the skin of the patient.

In some embodiments, the system may further include a contact sensor coupled with the controller. The controller may be configured to return the cooling applicator of the treatment device toward an idle state based on a signal from a contact sensor indicating removal of the cooling applicator from the skin of the patient.

Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The invention will be better understood upon reading the following description and examining the figures which accompany it. These figures are provided by way of illustration only and are in no way limiting on the invention.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
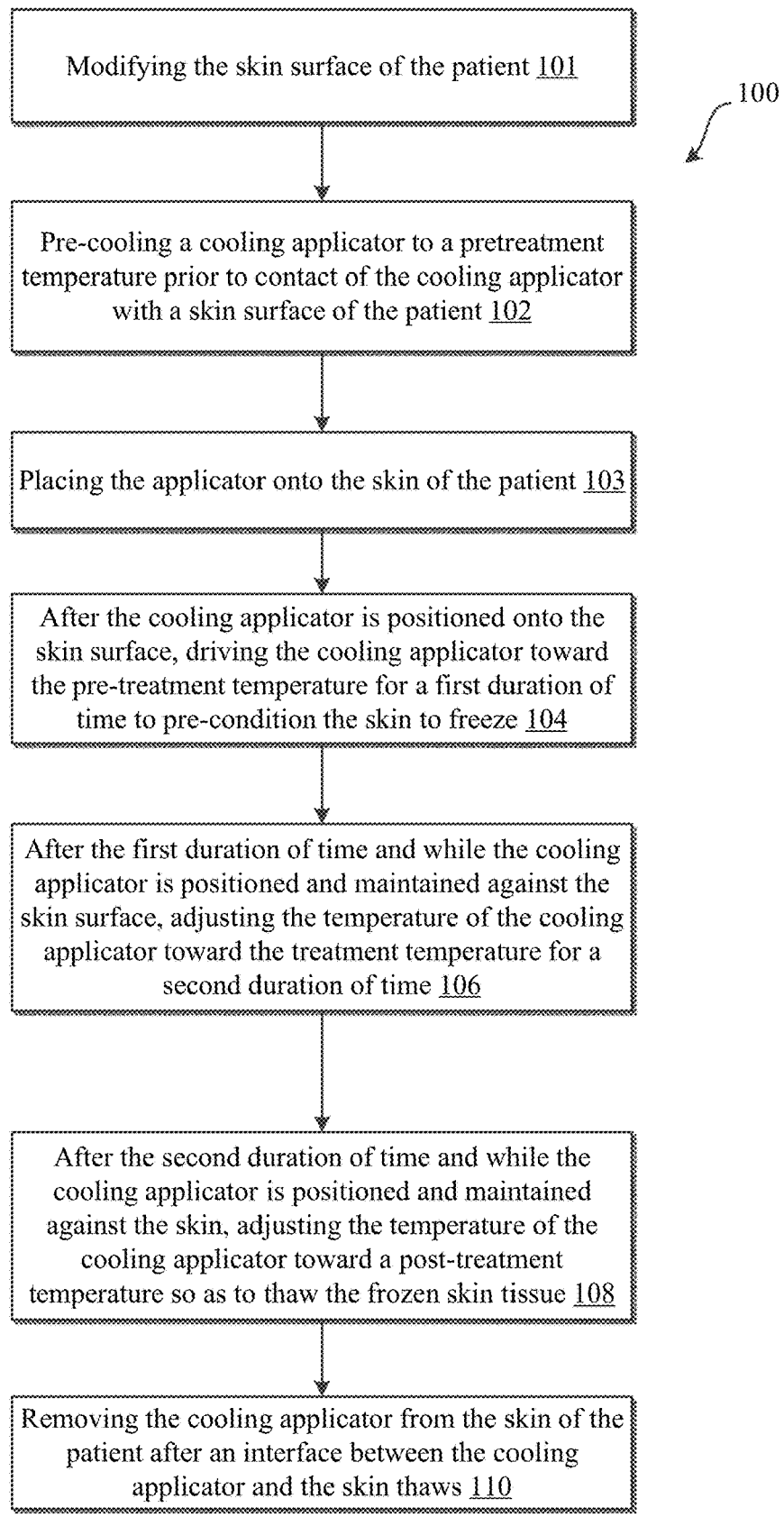
FIG. 1 illustrates an exemplary treatment method according to some embodiments of the present invention.

As set forth above, some embodiments of the present invention may be directed to techniques to affect melanocytes and/or keratinocytes of a patient. For example, some embodiments may be directed to methods and systems for reducing skin pigmentation by cooling the skin of a patient. In some embodiments it may be beneficial to freeze the skin. Additionally, it may be advantageous to freeze the skin in a more controllable and consistent manner. The freezing event, although it may not be required, has been shown to have an effect on both the desired outcome of reduced pigmentation, but also the short term side effects of epidermal necrosis and in some cases prolonged erythema and hyperpigmentation. In previous studies, the timing of skin freezing has been found to be inconsistent. Different results (time to freezing, or lack of freezing) have been seen when replicates of the same treatment parameters are performed. Accordingly, some embodiments of the present invention provide increased control over the occurrence of freezing in the skin of a patient and may limit supercooling in the skin. Methods and systems described herein may thus increase the chance, predictability, and/or consistency of freezing in the skin of a patient (e.g., repeatable freezing at certain temperatures and/or cooling rates) and may thereby provide additional control over a duration of skin freezing during treatment. Some embodiments may be directed to limiting supercooling of the skin of a patient during a cooling treatment. Supercooling of the skin may be cooling of the skin below the water freezing point without solidification or crystallization of water in the skin.

A number of cooling systems have been developed for lightening the pigmentation of skin (see e.g., U.S. Patent Publication 2011/0313411 filed Aug. 7, 2009; U.S. Patent Publication 2014/0303696 filed Nov. 16, 2012; U.S. Patent Publication 2014/0303697 filed Nov. 16, 2012; U.S. Patent Publication 2015/0223975 filed Feb. 12, 2015 and U.S. patent application Ser. No. 15/257,827 filed Sep. 6, 2016, the contents of which are incorporated herein by reference in their entirety). In general, the systems provide a cooling contact surface configured to contact and freeze skin tissue (typically the superficial layer of skin down to the dermal/epidermal junction). The freezing of the skin tissue may decrease melanin production, decrease melanosome production, destroy melanoncytes, and/or inhibit transfer of melanosomes into keratinocytes in the lower region of the epidermal layer, thereby leading to skin lightening (i.e., hypopigmentation) for a period of time or permanently.

Some treatments may use relatively modest skin cooling to temperatures in the range of 0° C. to −20° C. over fairly short times frames, e.g., as short as 15 seconds or less and up to 2 minutes or more. In some embodiments, skin cooling may be performed by controlling the temperature of an aluminum plate (e.g. cooler or cooling applicator) and applying the cooler directly to the skin—thereby cooling the skin through thermal conduction from the skin to the cooler.

It has been found that controlling certain aspects of the interface between the cooling applicator and the skin may modify freezing behavior of the skin. For example, freezing may be triggered more reliably by specifying and maintaining a fluid at the interface between the applied applicator and the skin. Water is a coupling fluid that can be used to reduce the thermal contact resistance between the applicator and the skin and thereby improve cooling. Water can either be pure or contain a thickening agent to increase viscosity. Water has a freezing point generally of 0° C. which is very near that of the tissue. However water, particularly in small quantities, has been known to supercool below its typical freezing point, particularly at slower rates of cooling. Substances can therefore be mixed with the water to minimize the chance of supercooling but not significantly decrease the freezing point, which would be undesirable. Some such substances are inorganic materials such as soot, dust, fine particulates, or silver iodide crystals. Other materials that can be added are organic substances such as proteins, lipoproteins, bacteria or fungi. Long chain aliphatic alcohols and amino acids, such as 1-aspartic acid can also be added to the water, or another fluid with a freezing point near 0° C., to reduce the chance of supercooling in the tissue.

Freezing can additionally be encouraged by applying a carrier at the interface, such as a saturated piece of gauze or another woven or non-woven material. The carrier should occupy some volume, but allow the free transfer of water across it. This carrier will ensure a sufficiently large and uniform quantity of water or other fluid is present at the interface which facilitates freezing of the skin.

Supercooling can be minimized by presenting a seed crystal which serves as a nucleation source for water at or just below its freezing point. One of the best seed crystals is frozen water, or ice. To ensure the applicator has ice crystals, which are available from the air even when the humidity is relatively low, the surface roughness of the applicator surface can be increased. By providing nooks and crannies on the applicator surface, the surface area of the applicator is increased and recessed areas will retain ice crystals even after being cleaned with alcohol or other cleaners. In addition these recessed areas prevent the ice from melting when first applied to warm skin. It may be helpful to allow the applicator surface to dwell at a temperature below freezing for a period of time prior to the treatment to ensure water from the air freezes on its surface. Alternately it can be sprayed with a mist of water or other liquid, which will freeze on its surface prior to the treatment.

Other mechanisms to trigger ice nucleation in a supercooled medium include vibration or other mechanical perturbations, and ultrasound or acoustic irradiation. The design of the cooler may include a vibrating element to induce freezing at some point in the cooling cycle. Ultrasound or acoustic transducers may also be incorporated in the system design to control the nucleation event.

Once ice starts to form at the interface it then needs to propagate into the skin. The epidermis is generally impervious to water, although there are specialized areas such as sweat glands that are specifically designed to control the flow of moisture across this barrier. It may be however that ice propagation is limited across the epidermis as the skin is cooled which could result in supercooling in the tissue. To prevent this, small holes can be made in the epidermis to allow ice to freely propagate across this barrier. Holes can be initiated by abrasions with a rough cloth or brush, with a microderm abrasion roller or system, with a laser, or with a number of additional techniques. Further details of methods and devices for controlling aspects of the interface between the cooling applicator and the skin are described in U.S. patent application Ser. No. 15/257,827, the entire contents of which were previously incorporated by reference, and which may be used with aspects of the disclosure described herein.

In addition to controlling aspects of the interface between the cooling applicator and the skin, it has been found that the freezing behavior (frequency and time to freeze) can be modified by adjusting the thermal parameters of the cooling applicator. Accordingly, in some aspects of the invention, a method of treating the skin may be provided where the thermal parameters of the cooling applicator are adjusted during treatment. For example, FIG. 1 illustrates an exemplary treatment method 100 according to some embodiments. The method 100 may include modifying the skin of the patient in a manner described in U.S. patent application Ser. No. 15/257,827, previously incorporated by reference. For instance, in some embodiments, the method 100 may start by placing small holes in the skin. For example, a 0.3 mm, a 0.25 mm, or a 0.5 mm dermaroller may be used to place small holes in the epidermis. This may allow the subsequently generated ice to freely propagate across the stratum corneum. In prior studies, the stratum corneum appeared to create a barrier to ice propagation and although freezing occurred at the interface, the skin would freeze at a variable and unpredictable times even with consistent treatment conditions.

The method 100 may further include pre-cooling a cooling applicator to a pretreatment temperature prior to contact of the cooling applicator with a skin surface of the patient 102. After pre-cooling the cooling applicator to the pretreatment temperature, the applicator may be placed onto the skin of the patient 103. After the cooling applicator is positioned onto the skin surface, the cooling applicator may be driven toward the pre-treatment temperature for a first duration of time to pre-condition the skin to freeze 104. After the first duration of time and while the cooling applicator is positioned and maintained against the skin surface, the temperature of the cooling applicator may be adjusted toward the treatment temperature for a second duration of time 106. After the second duration of time and while the cooling applicator is positioned and maintained against the skin, the temperature of the cooling applicator may be adjusted toward a post-treatment temperature so as to thaw the frozen skin tissue 108. Thereafter, the cooling applicator may be removed from the skin of the patient after the interface between the cooling applicator and the skin thaws 110.

It has been found that by initially applying a colder temperature, therefore setting up a larger temperature gradient between the cooler and the skin, the skin can be made to freeze more consistently. With other conditions being equal, applying a colder temperature of −5° C. to the skin will cause freezing more consistently over a shorter period of time than applying a temperature of −2° C. A temperature of −10° C. will freeze more consistently and more quickly than a temperature of −5° C. and a temperature of −20° C. will freeze more consistently and more quickly than a temperature of −10° C. While colder temperatures will freeze skin more consistently and more quickly, it may not be desirable to apply such a low temperature to the skin for the duration of the treatment as lower temperatures and/or longer durations may lead to increased adverse side effects, such as hyperpigmentation. Therefore, the cooler may be applied at a first colder temperature (or a pre-treatment or pre-conditioning temperature) to trigger freezing and then may be adjusted to a higher/warmer temperature that is still below the freezing point of the skin tissue for the duration of the treatment.

Additionally by precooling the cooling applicator prior to skin contact, ice crystal formation on the cooling applicator through moisture in the air or through water application directly to the cooling applicator (e.g., misting or the like) may be provided. Further, with colder precooling temperatures, it will be less likely that ice crystals that have formed on the surface of the applicator melt when the applicator is placed in contact with the patient skin. Accordingly, ice formation on the cooling applicator may remain after initial contact with the patient skin to seed ice formation at the interface and into the skin.

If the precooling temperature is too warm, the ice formed on the cooling applicator may melt upon the initial contact between the applicator and the skin and may be unavailable to seed ice formation at the interface and into the skin. Instead the water may return to and stay in the liquid state and may supercool for some variable amount of time, thereby reducing the consistency of freezing.

In some embodiments, the cooling applicator is pre-cooled 102 to a temperature between −10° C. and −20° C. Optionally, the cooling applicator is pre-cooled 102 to between −12° C. and −18° C., for example −15° C. In some embodiments, the cooling applicator is pre-cooled 102 to a temperature of −15° C. or colder.

As mentioned above, after contact with a skin of the patient, the temperature of the cooling applicator may increase due to heat transfer from the skin of the patient. Accordingly, in some embodiments, the cooling applicator is driven toward the pre-treatment temperature for a duration of time after the initial contact 104. The duration of time where the cooling applicator is driven toward the pre-treatment temperature may be less than five seconds in some embodiments (e.g., 0-3 seconds or the like). In some embodiments, the duration of time may be a preset parameter of a preprogrammed treatment cycle. The colder pre-treatment temperature may provide the larger temperature gradient between the cooling applicator and the skin and may thereby condition the skin to freeze in a more consistent manner and/or maintain previously seeded ice crystals at the interface between the cooling applicator and the skin.

The thermal effusivity of the interface material and the applicator material may come into play here. If the applicator has a high thermal effusivity relative to the interface, its temperature may remain relatively stable (e.g. it doesn't warm much) and therefore it is able to initiate freezing because any small ice crystals that have formed on its surface may stay frozen. The thickness of the applicator material also comes into play. A thick material of a high thermal effusivity maintains a relatively constant temperature, whereas a thin material backed by another material of a lower thermal effusivity would warm significantly. In some embodiments, the applicator may comprise an aluminum surface having an approximately 0.5 inch thickness. Alternately, the applicator may have a cooling surface with a thickness of 0.25 inches or less combined with a more powerful TEC that is able to respond to high transient heat loads. The cold plate may also be made out of copper or another material with a suitably high thermal effusivity.

After the applicator is applied, it is driven toward the pretreatment temperature for a short period of time to ensure sufficient energy is extracted from the interface to initiate freezing then the applicator may be adjusted or warmed to a second temperature (or treatment temperature) 106, warmer than the first temperature. The treatment temperature, while warmer than the pre-treatment temperature, is preferably below a skin freezing temperature, at least in certain embodiments. In some embodiments, the treatment temperature is between −2° C. to −12° C., or between −2° C. and −10° C., for example −8° C. to −10° C. The second warmer treatment temperature allows the treatment effect to be modulated (the warmer the temperature the less the effect) and reduce side effects (more prevalent at colder temperatures). The applicator may then be driven toward the second temperature for a period of time sufficient to achieve the desired treatment effect but avoid undesired side effects. In some embodiments, the temperature of the cooling applicator may be adjusted toward the treatment temperature for a duration between 10-30 seconds while the applicator is positioned against the skin. In some embodiments, the duration of applying the second treatment temperature may be a preset parameter of a preprogrammed treatment cycle.

As set forth above, the duration of time where the cooling applicator is driven toward the treatment temperature may be a predetermined parameter that is programmed into a preset treatment cycle. In some embodiments, the duration of time where the cooling applicator is driven toward the treatment temperature may be variable and may, in certain embodiments, depend on the initiation of a skin freeze. For example, in some embodiments, a sensor may be incorporated to detect a freezing of a tissue proximal to the applicator. After the freeze is detected, the more moderate (warmer) second freezing temperature may be applied for a preset duration of time following the detection of the freeze. Such an embodiment may modulate the treatment effect by maintaining the tissue in the frozen state for a pre-specified duration of time.

In certain embodiments, the freeze detection sensor may be a temperature sensor that is configured to detect the occurrence of local tissue freezing. The temperature detected by a temperature sensor may correspond to the temperature of the cooling applicator that it is in contact with. When the applicator is placed on the skin surface, the detected temperature will rise as the bottom surface of the applicator is warmed slightly by the skin. As conductive cooling of the skin by the applicator proceeds, the measured temperature will then decrease. The rate and extent of such decrease can depend on several factors, e.g., the initial temperature, material, and geometry of the applicator, the efficiency of the cooling arrangement used to cool the applicator, etc. When tissue freezing occurs proximal to the bottom surface of the applicator, a slight temporary increase in local temperature may be detected that arises from latent heat released during the freezing phase transformation. The detected temperature may then continue to decrease as further cooling of the frozen tissue proceeds. Accordingly, a "bump" detected in the temporal cooling curve by a temperature sensor can also indicate the occurrence of local tissue freezing. U.S. Patent Publication 2014/0303696 and U.S. Patent Publication 2014/0303697, previously incorporated, describe other freeze detection sensors that may be incorporated with embodiments of the present disclosure for the purpose of determining the initiation of a skin freeze.

Similarly, the duration of time where the cooling applicator is driven toward the pre-treatment temperature after initial contact may be variable and may, in certain embodiments, depend on the initiation of a skin freeze. For example, the freeze detection sensor may be incorporated to detect the freezing of the tissue proximal to the applicator. After the freeze is detected, the cooling applicator may cease to be driven toward the pre-treatment temperature and the more moderate (warmer) second freezing temperature may be applied thereafter.

After the duration of cooling treatment, the temperature of the cooling applicator may be adjusted toward a post-treatment temperature 108. In some embodiments, the post treatment temperature stops treatment and may be above 0° C. to thaw the interface or otherwise unstick the cooling applicator from the skin. In some embodiments, the post-treatment temperature is between 0° C. and 10° C. (e.g., 5° C. or the like), or between 0° C. to 40° C. In some embodiments, the applicator may be maintained against the skin of the patient for upwards of 30 seconds after the treatment. After the interface thaws, the applicator may be removed from the skin 110. It should be understood that the times and temperatures are not critical. In some embodiments, the goal is to unfreeze the tissue in a relatively short period of time and to release the applicator from the tissue.

Figure 2:
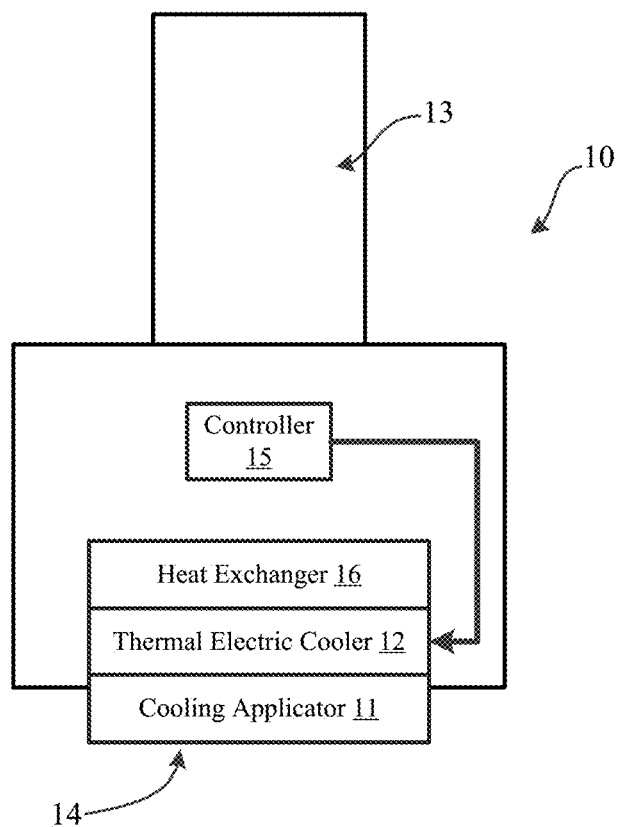
FIGS. 2-2E illustrate cross-sectional side views of exemplary apparatuses that can be used to produce hypopigmentation in a skin tissue according to some embodiments of the present invention.

FIG. 2 illustrates an exemplary cross-sectional side view of an exemplary apparatus 10 that can be used to produce hypopigmentation in a skin tissue according to some embodiments of the present invention. The exemplary apparatus 10 can include a cooling applicator 11 provided in a thermal communication with a thermoelectric cooler 12. A heat exchanger 16 may be thermally coupled with the thermoelectric cooler 12 on a side opposite from the cooling applicator 11. In certain exemplary embodiments, the cooling applicator 11 and the cooling arrangement 12 can be formed at least in part from a single material. A controller 15 can be provided and used to control certain aspects of the thermoelectric cooler 12, e.g., temperature, timed shutoff, etc., to perform aspects of method 100. The thermoelectric cooler 12, controller 15, and/or cooling applicator 11 can optionally be provided within or affixed to a housing or handpiece 13, as shown in FIG. 2, e.g., to facilitate handling and positioning of the apparatus 10. The exemplary apparatus 10 shown in FIG. 2 is not necessarily drawn to scale. For example, the relative dimensions of the thermoelectric cooler 12 and cooling applicator 11 are not limited to the proportions illustrated in the FIG. 2. In further exemplary embodiments of the present disclosure, the cooling applicator 11 can be larger or smaller in width or cross-sectional area as compared to the dimensions of the thermoelectric cooler 12.

The cooling applicator 11 can include a distal (contact) surface 14 that is configured to contact a skin surface. The distal surface 14 can be substantially flat. In further exemplary embodiments of the present disclosure, the distal surface 14 can be convex or concave to better match the local shape of skin tissue being treated and/or to provide good thermal contact with the skin surface when the apparatus 10 is placed on the area of the skin to be treated. In still further exemplary embodiments of the present disclosure, the cooling applicator 11 can be detachable from the thermoelectric cooler 12, e.g., so that a plurality of cooling applicator 11 having different sizes, shapes, and/or surface features as described herein can be used with a single thermoelectric cooler 12.

The distal contact surface 14 can have a large width or diameter configured to contact the surface of a region of skin, e.g., a diameter or width that is greater than about 3-10 cm, or greater than about 5 cm, to facilitate treatment of large areas of skin. In further embodiments, the width of the distal surface 14 can be small, e.g., on the order of 1-2 cm or less which may facilitate improved temperature control and/or treatment of particular features on the skin.

The cooling applicator 11 can be formed from a metal or a metal alloy, or another material having a high thermal effusivity, e.g., such that values of these thermophysical properties are greater than the corresponding values for skin tissue. The thermal effusivity c is equal to the square root of the product of a material's thermal conductivity and its volumetric heat capacity. The thermal effusivity is a measure of the ability of a material to exchange heat with its surroundings and to maintain a consistent temperature as it does so. For example, the interface temperature Ti where two semi-infinite materials at temperature T1 and T2, respectively, are brought into contact will depend on their relative effusivities, $\epsilon 1$ and $\epsilon 2$, as $Ti=T1+(T2-T1)\times[\epsilon 2/(\epsilon 2+\epsilon 1)]$. Accordingly, e.g., with $\epsilon 2>>\epsilon 1$, the interface temperature where the two materials are in contacts will remain close to T2 as heat flows from one to the other. In this manner, the surface of a first material will be cooled down close to the temperature of a second material having a much higher thermal effusivity when the second material is brought into contact with the first material.

For example, the cooling applicator 11, at least in part or wholly, can be made of brass, copper, silver, aluminum, an aluminum alloy, steel, graphite, diamond, diamond-like carbon, other materials which are used in conventional contact cryoprobes, or combinations thereof. For example, the cooling applicator 11 can be formed, wholly or at least in part, from materials having a much higher thermal conductivity than the skin tissue, and can be used to facilitate an extraction of heat from the portion of the tissue contacted by the distal surface 14 of the cooling applicator 11. Further, materials having a much higher thermal effusivity than the skin tissue, e.g. at least about 10 times the thermal effusivity of skin can be more readily maintained at a cold temperature. Such high-effusivity materials thereby may extract heat more effectively from the portion of tissue contacted by the cooling applicator 11 than materials having lower thermal effusivities, and facilitate a better control of the tissue temperature at a contact interface.

In certain exemplary embodiments of the present disclosure, the distal contact surface 14 of the cooling applicator 11 can be smaller in area than the proximal end of the cooling applicator 11 that contacts the thermoelectric cooler 12. Such geometry can provide certain advantages. For example, the narrower or tapered distal end of the cooling applicator 11 can facilitate a more precise placement of the distal surface 14 on a particular location of the skin surface to be cooled, e.g., while reducing visual obstruction by the housing 13. Further, the relatively larger proximal end of the cooling applicator 11 can provide a larger area that can be directly cooled by the thermoelectric cooler 12 to facilitate increased extraction of heat from the smaller distal contact surface 14. In certain embodiments, the area of the proximal end of the cooling applicator 11 can be at least twice as large as the area of the distal contact surface 14, e.g., 3-5 times as large.

Figure 2A:
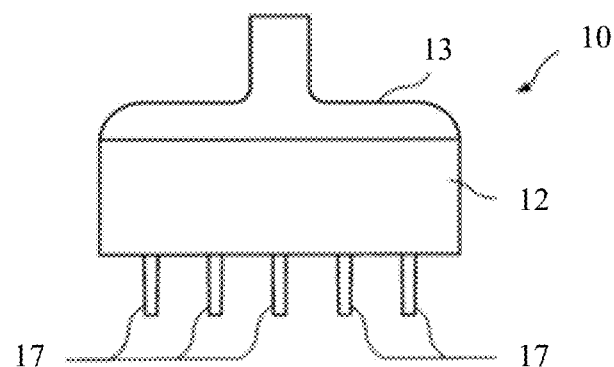
Figure 2B:
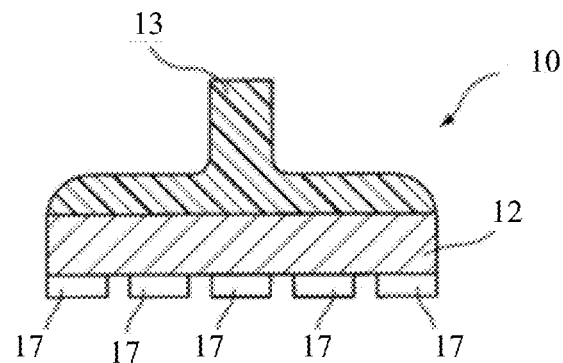
Figure 2C:
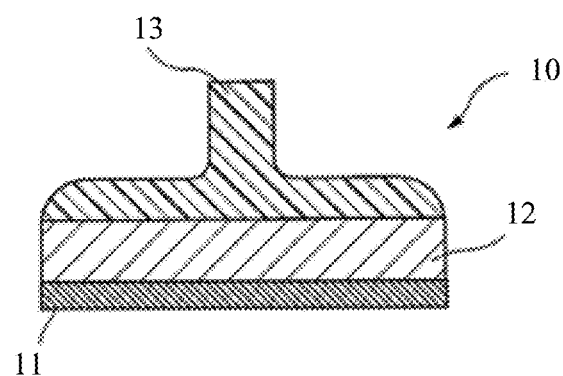
Figure 2D:
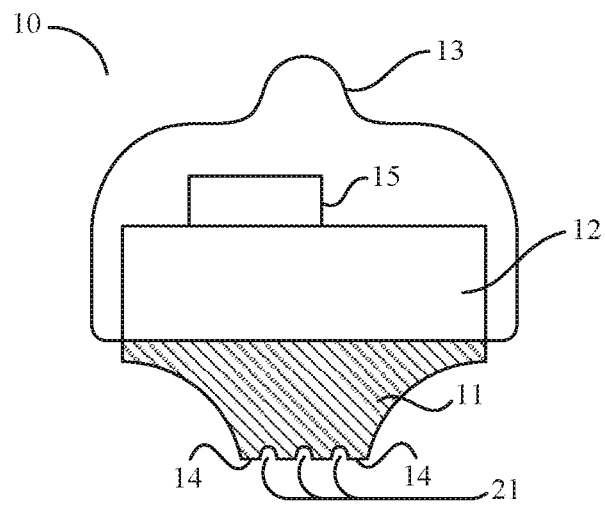
Figure 2E:
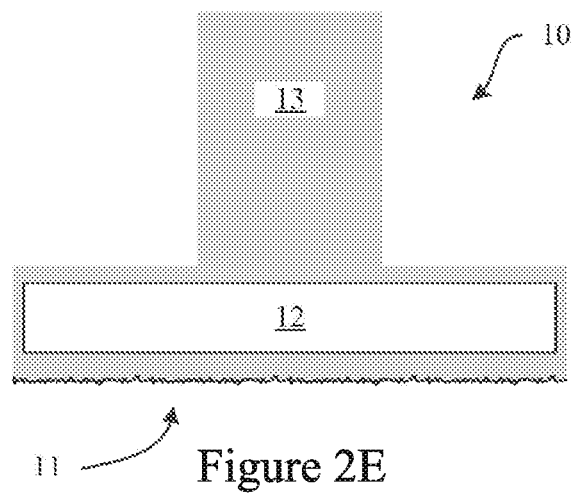

In some embodiments, the distal surface 14 of the cooling applicator 11 can be provided with a plurality of protrusions, similar to those described in U.S. Patent Publication 2011/0313411 or U.S. Patent Pub. 2014/0303697, previously incorporated by reference. FIGS. 2A and 2B illustrate exemplary treatment devices with protrusions 17 for discontinuous treatment of a region of skin which may provide cooling treatments according to the present disclosure. Alternatively, as mentioned above, the distal surface may be flat or rounded to provide a continuous contact surface similar to the applicators described in U.S. Patent Publication 2014/0303696. FIG. 2C illustrates an exemplary treatment device with a flat surface for continuous contact and treatment of a region of skin which may provide cooling treatments according to the present disclosure. In still further embodiments, the distal surface 14 may include dimples similar to the applicators described in U.S. Patent Publication 2015/0223975. FIG. 2D illustrates an exemplary treatment device with a dimpled surface 21 for treatment of a region of skin which may provide cooling treatments according to the present disclosure. Optionally, the distal surface 14 may be roughened or knurled similar to the applicators described in U.S. Provisional Patent Application 62/214,446. FIG. 2E illustrates an exemplary treatment device with a roughened surface for treatment of a region of skin which may provide cooling treatments according to the present disclosure.

Figure 3:
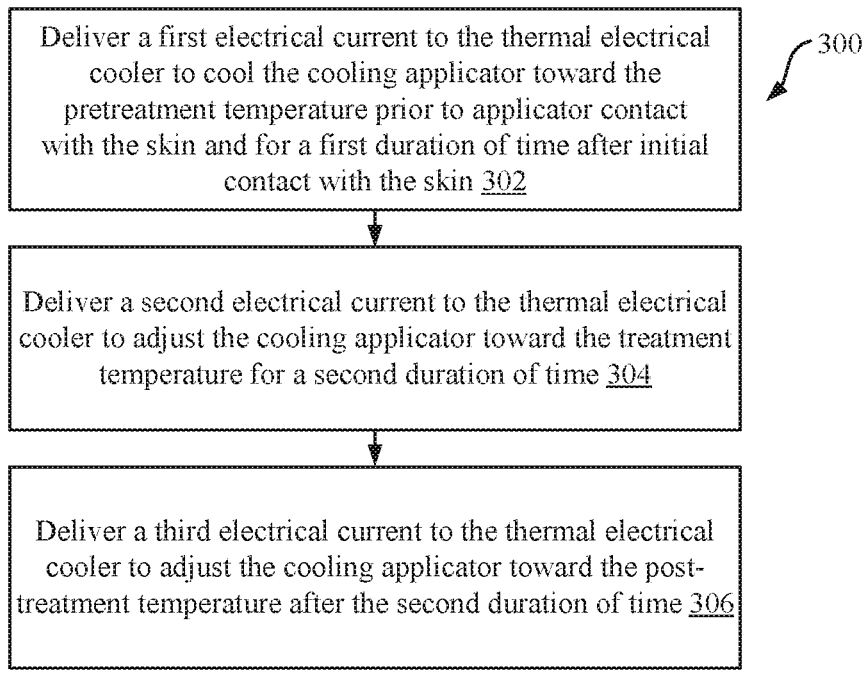
FIG. 3 illustrates an exemplary method for delivering treatment cycles according to some embodiments.

As set forth above, a controller 15 may be provided to control the thermoelectric cooler 12. FIG. 3 illustrates an exemplary method 300 for delivering treatment cycles according to some embodiments. In some embodiments, the controller 15 may be configured to control the thermoelectric cooler 12 or other cooling arrangement to provide a cooling treatment cycle that performs certain aspects of method 100. For example, the controller 15 may deliver a first electrical current to the thermoelectric cooler 12 to pre-cool the cooling applicator 11 to a pre-treatment temperature prior to contact with the skin of the patient 302. The first electrical current may be delivered to the thermoelectric cooler 12 to cool the cooling applicator toward the pre-treatment temperature for a first duration of time after the cooling applicator is placed against the skin of the patient 302. After the first duration of time and while the cooling applicator is held against the skin of the patient, a second electrical current may be delivered to the thermoelectric cooler 12 to adjust the temperature of the cooling applicator 11 toward a treatment temperature that is higher (warmer but generally below a temperature for skin freezing) than the pre-treatment temperature for a second duration of time 304. After the second duration of time and while the cooling applicator is held against the skin of the patient, a third electrical current may be delivered to the thermoelectric cooler 12 to adjust the temperature of the cooling applicator 11 toward a post-treatment temperature that is higher than the treatment temperature for a third duration of time 306.

In some embodiments, a temperature sensor may be provided to provide a signal to the controller 15 that is associated with a temperature of the cooling applicator 11. The signal from the temperature sensor may indicate when the cooling applicator 11 has reached the pre-treatment temperature and is ready for application to the skin of the patient. In some embodiments, the controller 15 may provide a user perceptible signal to indicate that the device 10 is ready for application to the skin of the patient. The user perceptible signal may be audio, visual, or haptic or the like.

The controller 15 may also, in response to the temperature signal, automatically adjust the current and/or power delivered to the thermoelectric cooler 12 to drive the cooling applicator toward the desired temperature. Depending on the responsiveness of the control system, in some embodiments, the current delivered to the thermoelectric cooler may be temporarily reversed during transition from the delivery of the first electrical current to the delivery of the second electrical current. Similarly, in some embodiments, the current delivered to the thermoelectrical cooler may be temporarily reversed during transition from the delivery of the second electrical current to the delivery of the third electrical current.

Optionally, in some embodiments, the power delivered to the thermoelectric cooler may be reduced or turned off during transition from the delivery of the first electrical current to the delivery of the second electrical current. Similarly, in some embodiments, the power delivered to the thermoelectric cooler may be reduced or turned off during transition from the delivery of the second electrical current to the delivery of the third electrical current.

In some embodiments, the adjustments to the thermoelectric cooler 12 after the first duration of time and the second duration of time may be automatic as well. For example, a user may actuate a switch when the cooling applicator is applied against the skin of a patient. Actuation of the switch may signal the start of a treatment cycle to the controller 15. Thereafter the controller 15 may adjust the current and/or power delivered to the thermoelectric cooler 12 in a pre-programmed manner to adjust the temperatures at the preset times.

In further examples, a contact sensor may be provided that provides a signal to the controller 15 that indicates that the cooling applicator 11 is placed against the skin of the patient. Thereafter, the controller 15 may automatically initiate a cooling treatment cycle (e.g., where the controller 15 automatically adjusts temperatures in which the cooling arrangement 12 is driven toward after the first and second durations of time). The contact sensor may be a force sensor, optical sensor, IR sensor, temperature sensor, or a sensor that measures a change in the electrical properties of the plate and interface such as a change in resistance, capacitance, or the like.

For example, in some embodiments, a temperature sensor may be provided. The treatment cycle may be initiated when the temperature sensor detects an increase in temperature from the pre-treatment temperature. The increase in temperature may be due to contact with the skin of the patient and heat transfer from the skin into the cooling plate. Thereafter, the treatment cycle may be triggered (e.g., automatically) by the increase in temperature. In some embodiments, the temperature signal from the sensor may be averaged over a duration of time (e.g., 1-2 seconds) or moving time window, and then compared to the threshold. This may help reduce unintended triggers due to transient drops or spikes in temperatures sensed.

In some embodiments, a force sensor may be provided that detects when the cooling applicator is contacted with the skin based on a force experienced at the cooling applicator. An increase in force sensed may indicate that the applicator is being pressed against the skin of the patient. Thereafter, the treatment cycle may be triggered (e.g., automatically) by the increase in force sensed. Similarly, a negative force sensed may indicate that the applicator is still frozen/attached to the patient skin during an inadvertent device removal. A warning to the end user could then be triggered to prevent potential damage to the patient skin. In some embodiments, the force signal from the sensor may be averaged over a duration of time (e.g., 1-2 seconds) or moving time window, and then compared to the threshold. This may help reduce unintended triggers due to transient drops or spikes in forces sensed.

The initial contact of the cooling apparatus with the skin may also be detected based on a change in the amount of power delivered to a thermoelectric cooler. For example, when the apparatus makes initial contact with the skin of the patient, a temperature of the thermoelectric cooler may increase due to heat transfer from the skin of the patient. Accordingly, the controller 15, using temperature feedback, may deliver additional power to the thermoelectric cooler to maintain the thermoelectric cooler at a desired temperature. The increase in power delivered to the thermoelectric cooler may trigger the initiation of the treatment cycle. Alternately, the contact may be detected by observing a change in the measured temperature of the cold plate.

Alternately, the treatment may be triggered by a mechanical switch that is user actuated when the applicator is placed in contact with the skin. Accordingly, one or more signals from contact sensors, power consumption measurements, heat flux measurements, or other measured signals may also modify treatment parameters/algorithm during treatment.

Figure 4:
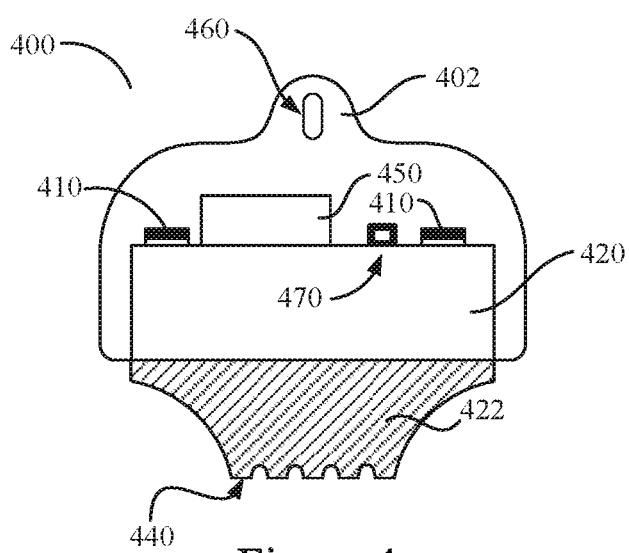
FIG. 4 illustrates a cross-sectional view of an exemplary treatment device with one or more force sensors according to some embodiments.

In some embodiments, the treatment device may be provided with one or more force sensors, as shown in the exemplary cross-sectional configuration of FIG. 4. The exemplary apparatus 400 can include a handle 402, a cooling arrangement 420, and an optional cooling plate 422 provided on a lower surface of a cooling arrangement 420. The force sensor(s) 410 can be used to detect force which may be translated into a pressure based on the application surface size of the cold plate thereby communicating, e.g., a contact pressure between the contact surface 440 of the apparatus 400 and the skin or tissue surface during operation of the apparatus 400. Such pressure detection can be useful, e.g., to ensure a sufficient or appropriate pressure is applied to facilitate good thermal contact between the contact element 422 and the tissue being treated. A contact pressure of a few PSI or more (e.g., greater than the systolic pressure in a blood vessel, for example about 2.5 PSI or more) can also produce some local blanching or restriction of blood flow near the tissue surface. Local blanching can reduce the heat transfer to the local tissue by flowing blood, and thereby improve the cooling or heat extraction by the apparatus 400 near the tissue or skin surface.

The force sensor(s) 410 can include any conventional components that can be used to detect force such as, e.g., a piezoelectric material, a piezoresistive strain gauge, a capacitive or inductive sensor, pressure sensitive inks, etc. One or more force sensors 410 can be provided in the apparatus 400. Their number, type and/or locations of the force sensors 410 can be selected based on several factors including, e.g., reliability of the detected contact force. For example, the force sensor 410 can be small, have a low thermal mass and/or have a high thermal conductivity to minimize or avoid any reduction in the heat transfer characteristics of the apparatus 400.

The location of the one or more force sensors 410 can be selected to provide an accurate indication of the contact pressure between the contact surface 440 and the skin surface during use of the apparatus 400. For example, one or more force sensors 410 can be provided between an upper portion of the cooling arrangement 420 and the handle 402, as shown in FIG. 4, if the cooling arrangement 420 and handle 402 are in good mechanical contact. This exemplary configuration can provide force sensing capabilities while avoiding any reduction of the heat flow or transfer between the cooling arrangement 420 and the skin surface. In further exemplary embodiments of the present disclosure, one or more force sensors 410 can be provided between the cooling arrangement 420 and the contact element 422, on the contact surface 440 of the contact element 422, within the contact element 422, or any combination of such locations.

A force indicator 460 can be provided on or near the apparatus 400. Such force indicator can include a digital or analog readout of the detected contact force, an indicator light that can turn on/off or change color to indicate when the contact force is within or outside a particular force range or above/below a particular limit, an audible signal, etc.

The force indicator can be used to provide or otherwise transmit a signal to the operator to ensure the presence of an appropriate contact force during use of the apparatus 400. This force-sensing feature can be used with any of the exemplary embodiments of the apparatus and method described herein.

Optionally, in some embodiments, the force sensor 410 may be coupled with the controller 450 and the duration of time where the cooling applicator is driven toward the pre-treatment and/or treatment temperature may be automatically modulated based on the force sensed by force sensor 410. For example, if the force sensor 410 senses a force below a certain threshold, a duration of time where the cooling applicator is driven toward the pre-treatment and/or treatment temperature may be adjusted (prolonged or adjusted). Similarly, if the force sensor 410 senses a force above a certain threshold, a duration of time where the cooling applicator is driven toward the pre-treatment and/or treatment temperature may be adjusted (e.g., prolonged or shortened). In some cases, the force will be normalized by the surface area of the contact surface resulting in a pressure. In some embodiments, a timer for the pre-treatment time or the treatment time may be paused when the pressure sensed is below the threshold and restarted when the pressure sensed rises above the threshold. Optionally, the timer for the pre-treatment time or the treatment time may be reset if the pressure sensed falls below the threshold. In further examples, the treatment time may be extended if the pressure drops below a threshold, for example 1 psi. Additionally, the treatment time may be extended if the pressure exceeds a threshold. These treatment times may be similarly modified based on thresholds of TEC power and/or measured heat flux.

In some embodiments, if a force sensor 410 senses a force outside of a desired range, a temperature of the cooling applicator may be adjusted. For example, in some embodiments, if the force sensor 410 senses a force below a threshold, controller 450 may adjust the cooling arrangement to deliver a colder temperature (during pre-treatment and/or treatment). Additionally, in some embodiments, if the force sensor 410 senses a force above a threshold, controller 450 may adjust the cooling arrangement to deliver a warmer temperature (during pre-treatment and/or treatment). In some embodiments, the signal from the sensor may be averaged over a duration of time (e.g., 1-2 seconds) or a moving time window, and then compared to the threshold. This may help reduce triggers due to transient drops or spikes in forces sensed.

Furthermore, in some embodiments, feedback from force sensor 410 may signal the end of a treatment cycle. For example, a pressure drop may be detected by force sensor 410, e.g., sensing a transition from 2-5 lbs. to about 0 lbs., which signals that the user (clinician or the like) has removed the apparatus from the skin of the patient. Thereafter, the controller 450 may reset the apparatus to a desired state or idle state. For example, in some embodiments, the controller 450 may control the cooling arrangement 420 to drive the contact surface 422 toward the pre-treatment temperature to prepare for the next cooling treatment application. Alternatively, in some embodiments, the controller 450 may cease power delivery to the cooling arrangement 420 when the force sensor 410 indicates that the contact surface 422 has been disengaged from the skin of the patient. While several aspects above have been generally described with use of a force sensor 410, it will be appreciated that other contact sensors or measured signals (e.g., heat flux measurement) may be used as discussed above. For example, spring-based contact sensor, infrared contact sensors, or the like may be used to sense the disengagement of the contact surface 422 from the skin of the patient so as to automatically trigger the return of the apparatus to a desired or idle state.

For embodiments utilizing a force sensor (e.g., sensor 410) for sensing when the apparatus is removed from the skin of the patient, it may be beneficial to utilize a signal from an orientation sensor 470 (e.g., an accelerometer or the like) to calibrate the pressure reading (e.g., to adjust for gravitational effects detected by the sensor). For example, when the apparatus 400 is oriented with the contact element 422 facing upward (i.e., opposite of what is illustrated in FIG. 4), force sensors 410 may sense the weight of cooling arrangement 420 and contact element 422. In the alternative, when the apparatus 400 is oriented with the contact element 422 facing downward (as illustrated in FIG. 4), force sensors 410 may not sense the weight of cooling arrangement 420 and contact element 422. Accordingly, in some embodiments, an accelerometer or other orientation sensor 470 may be provided to sense an orientation of the apparatus 400 to adjust for the gravitational or orientational effects to ensure that the controller 450 accurately determines when the apparatus is removed from the skin of the patient.

Additionally, in embodiments utilizing an orientation sensor, the controller coupled with multiple force sensors may be configured to determine when the apparatus is applied to the skin at an improper tilt or angle during a treatment cycle. When the tilt of the apparatus relative to the skin falls outside of a desired range, the precooling duration/temperature and/or treatment duration/temperature may be adjusted to account for the improper tilt of the apparatus relative to the skin. In some embodiments, the signal from the orientation sensor may be averaged over a duration of time (e.g., 1-2 seconds) and then compared to the tilt threshold.

Figure 5:
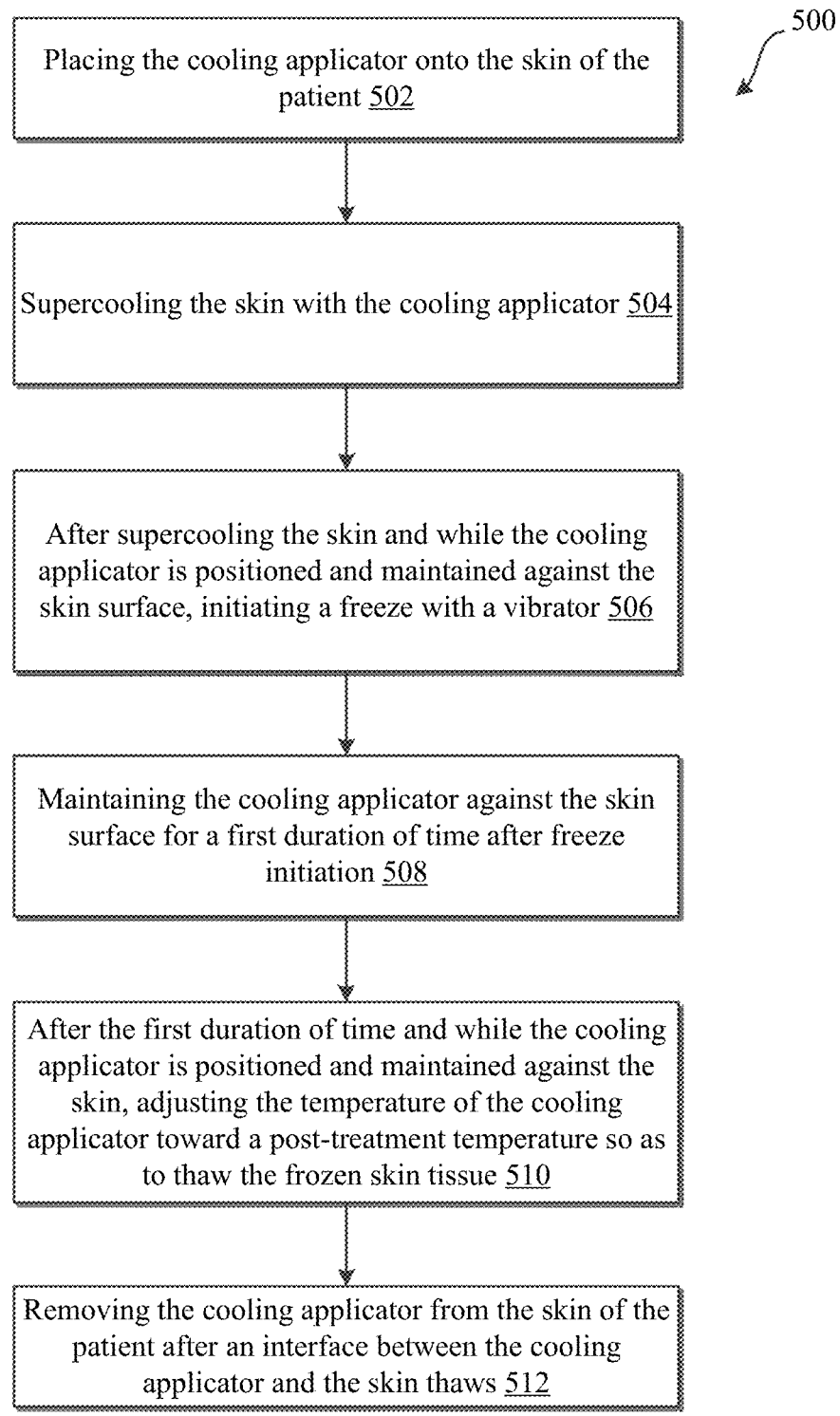
FIG. 5 illustrates another exemplary treatment method according to some embodiments of the present invention.

While many of the embodiments described above are generally discussed as limiting unintentional supercooling of the skin tissue, other embodiments of the present invention may intentionally supercool the tissue before initiating a freeze. For example, FIG. 5 illustrates another exemplary treatment method 500 according to some embodiments of the present invention. The method 500 may start with placing a cooling applicator onto the skin of the patient 502. The skin of the patient may then be intentionally supercooled with the cooling applicator 504. After supercooling the skin and while the cooling applicator is positioned and maintained against the skin surface, a freeze of the skin may be initiated with a vibrator 506. Thereafter, the cooling applicator may be maintained against the skin surface for a first duration of time after freeze initiation 508. After the first duration of time and while the cooling applicator is positioned and maintained against the skin, the temperature of the cooling applicator may be adjusted toward a post-treatment temperature so as to thaw the frozen skin tissue 510. After the interface between the cooling applicator and the skin thaws, the cooling applicator may be removed from the skin of the patient 512. For example, the skin might be supercooled for 20 seconds prior to inducing crystallization in the tissue. The tissue might then be held in the frozen state for an additional 15 seconds before rewarming to thaw the tissue. Without being bound by theory, the structure of the ice crystals change depending on the level of supercooling. In addition, the crystallization happens more rapidly in supercooled tissue. Both the structure and the speed of formation of ice crystals in the skin may lead to a beneficial clinical outcome when induced in supercooled tissue. Finally, by initiating ice crystallization with an external stimulus, the treatment becomes more controllable and consistent.

Figure 6:
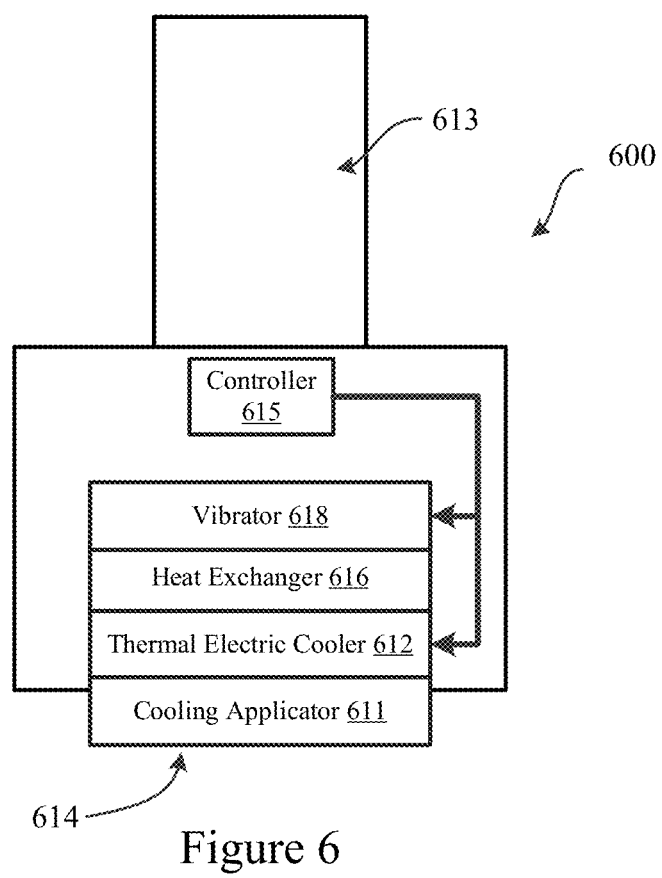
FIG. 6 illustrates another exemplary cooling apparatus that can be used to produce hypopigmentation in skin tissue according to some embodiments of the present invention.

FIG. 6 illustrates an exemplary cooling apparatus 600 that can be used to produce hypopigmentation in skin tissue according to method 500. The exemplary apparatus 600 can include a cooling applicator 611 provided in a thermal communication with a thermoelectric cooler 612. A heat exchanger 616 may be thermally coupled with the thermoelectric cooler 612 on a side opposite from the cooling applicator 611. In certain exemplary embodiments, the cooling applicator 611 and the cooling arrangement 612 can be formed at least in part from a single material. A vibrator 618 (e.g., acoustic transducer, ultrasound transducer, or the like) may be provided. In some embodiments, the vibrator 618 may be coupled with a distal side of the heat exchanger 616 so that the vibrator 618 is on the opposite side of the heat exchanger 616 relative to the thermal electric cooler. A controller 615 can be provided and used to control certain aspects of the thermoelectric cooler 612, e.g., temperature, etc. Additionally, the controller 615 may be coupled with the vibrator 618 to control the delivery (e.g., timing, power, frequency, etc.) of the ultrasound from the vibrator 618. The thermoelectric cooler 612, controller 615, vibrator 618, and/or cooling applicator 611 can optionally be provided within or affixed to a housing or handpiece 613, as shown in FIG. 6, e.g., to facilitate handling and positioning of the apparatus 600. The exemplary apparatus 600 shown in FIG. 6 is not necessarily drawn to scale.

For example, the relative dimensions of the thermoelectric cooler 612 and cooling applicator 611 are not limited to the proportions illustrated in the FIG. 6. In further exemplary embodiments of the present disclosure, the cooling applicator 611 can be larger or smaller in width or cross-sectional area as compared to the dimensions of the thermoelectric cooler 612.

The cooling applicator 611 can include a distal (contact) surface 614 that is configured to contact a skin surface. The distal surface 614 can be substantially flat. In further exemplary embodiments of the present disclosure, the distal surface 614 can be convex or concave to better match the local shape of skin tissue being treated and/or to provide good thermal contact with the skin surface when the apparatus 600 is placed on the area of the skin to be treated. In still further exemplary embodiments of the present disclosure, the cooling applicator 611 can be detachable from the thermoelectric cooler 612, e.g., so that a plurality of cooling applicator 611 having different sizes, shapes, and/or surface features as described herein can be used with a single thermoelectric cooler 612.

The distal contact surface 614 can have a large width or diameter configured to contact the surface of a region of skin, e.g., a diameter or width that is greater than about 3-10 cm, or greater than about 5 cm, to facilitate treatment of large areas of skin. In further embodiments, the width of the distal surface 614 can be small, e.g., on the order of 1-2 cm or less which may facilitate improved temperature control and/or treatment of particular features on the skin.

The cooling apparatus 600 may be configured to intentionally supercool the skin of the patient 504 for a period after initial contact with the skin of the patient. The cooling apparatus 600 may supercool the skin by gradually cooling the target surface to a first temperature, which could be between 0-5° C. or between 5-10° C. Possibly, after the freezing is initiated, the tissue could be warmed to a warmer temperature, still below the freezing point of tissue.

After supercooling the skin and while the cooling applicator 600 is positioned and maintained against the skin surface, a freeze of the skin may be initiated with a vibrator 506. The vibrations or other kinds of mechanical perturbations may help trigger or otherwise facilitate or promote ice nucleation in the fluid medium and/or the skin of the patient. Accordingly in some embodiments, the vibrator 618 may include one or more acoustic or ultrasound transducers (piezo elements or the like). The ultrasound transducer may deliver acoustic energy in the 20-100 kHz range. Optionally the vibrator 618 may be an electrical motor with an unbalanced mass on its drive shaft. While method 500 may be performed with device 600 which has an integrated vibrator 618, it should be understood that method 500 may be performed with a cooling apparatus and a separate vibration device in other embodiments of the present invention.

Thereafter, the cooling applicator 600 may be maintained against the skin surface for a first duration of time after freeze initiation 508. In some embodiments, the cooling applicator 600 may be driven towards a treatment temperature during the first duration of time. The treatment temperature may be below a skin freezing temperature, at least in certain embodiments. In some embodiments, the treatment temperature is between −2° C. to −12° C., or between −2° C. and −10° C., for example −8° C. to −10° C. In some embodiments, the cooling applicator 600 may be driven toward the treatment temperature for duration between 10-30 seconds while the applicator 600 is positioned against the skin. In some embodiments, the duration of applying the treatment temperature may be a preset parameter of a preprogrammed treatment cycle. In some embodiments, the duration of time may be variable and may be reset or paused based on signals from sensors (e.g., contact sensor, orientation sensor) or other measured signals similar to the embodiments described above.

After the first duration of time and while the cooling applicator is positioned and maintained against the skin, the temperature of the cooling applicator may be adjusted toward a post-treatment temperature so as to thaw the frozen skin tissue 510. In some embodiments, the post treatment temperature stops treatment and may be above 0° C. to thaw the interface or otherwise unstick the cooling applicator from the skin. In some embodiments, the post-treatment temperature is between 0° C. and 10° C. (e.g., 5° C. or the like), or between 0° C. to 40° C. In some embodiments, the applicator may be maintained against the skin of the patient for upwards of 30 seconds after the treatment. After the interface between the cooling applicator and the skin thaws, the cooling applicator may be removed from the skin of the patient 512. It should be understood that the times and temperatures are not critical. In some embodiments, the goal is to unfreeze the tissue in a relatively short period of time and to release the applicator from the tissue.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of altering pigmentation by reducing melanin in a skin tissue of a patient, the method comprising:
    pre-cooling a cooling applicator of a treatment device to a pre-treatment temperature prior to contact of the cooling applicator with a skin surface of the patient;
    after the cooling applicator is positioned onto and maintained against the skin surface, driving the cooling applicator toward the pre-treatment temperature for a first duration of time to condition at least an epidermal skin tissue to freeze while minimizing supercooling; and
    after the first duration of time and while the cooling applicator is positioned and maintained against the skin surface, controllably adjusting a temperature of the cooling applicator toward a treatment temperature for a second duration of time, the treatment temperature being configured to freeze at least a portion of the epidermal skin tissue in contact with the cooling applicator to alter a pigmentation by reducing melanin in the skin tissue, wherein the second duration of time is longer than the first duration of time, wherein the second duration of time begins after termination of the first duration of time.

2. The method of claim 1, wherein the treatment temperature is below 0° C.

3. The method of claim 2, wherein the pre-treatment temperature is in a range from −10° C. to −20° C.

4. The method of claim 3, wherein the treatment temperature is in a range from −2° C. to −10° C.

5. The method of claim 1, wherein the second duration of time is three to ten times longer in duration than the first duration of time.

6. The method of claim 5, wherein the second duration of time is less than 5 seconds.

7. The method of claim 1, wherein the second duration of time is a predetermined amount of time after an initiation of skin freezing.

8. The method of claim 1, further comprising adjusting the cooling applicator toward a post-treatment temperature that is higher than the treatment temperature after the second duration of time and while the cooling applicator is positioned and maintained against the skin surface so as to thaw frozen skin tissue.

9. The method of claim 8, wherein a thermoelectric cooler is thermally coupled with the cooling applicator, and wherein adjusting the cooling applicator toward the post-treatment temperature comprises reversing a current through the thermoelectric cooler.

10. The method of claim 8, wherein the post-treatment temperature is above 0° C.

11. The method of claim 10, wherein the post treatment temperature is less than 10° C.

12. The method of claim 8, wherein the cooling applicator is maintained in contact with the skin at the post-treatment temperature until the frozen skin tissue thaws.

13. The method of claim 1, wherein the pre-treatment temperature is colder than the treatment temperature.

14. A method of treating a skin of a patient, the method comprising:
    cooling a cooling applicator of a treatment device to a pre-treatment temperature prior to contacting the skin with the cooling applicator of the treatment device, the pre-treatment temperature configured to condition at least an epidermal portion of the skin to freeze;
    placing the cooling applicator onto the skin for a first duration of time while the treatment device cools the cooling applicator toward the pre-treatment temperature while minimizing supercooling;
    after the first duration of time, maintaining the cooling applicator against the skin for a predetermined second duration of time while the treatment device controllably adjusts the temperature of the cooling applicator toward a treatment temperature that is higher than the pre-treatment temperature and below freezing for the second duration of time that is longer than the first duration of time to freeze at least the epidermal portion of the skin for hypopigmentation, wherein the second duration of time begins after termination of the first duration of time;
    after the second duration of time, removing the cooling applicator from the skin of the patient after treating the skin toward the treatment temperature using the cooling applicator of the treatment device.

15. The method of claim 14, wherein the pre-treatment temperature is colder than the treatment temperature.

16. The method of claim 14, wherein the treatment temperature is below 0° C.

17. The method of claim 16, wherein the pre-treatment temperature is in a range from −10° C. to −20° C.

18. The method of claim 17, wherein the treatment temperature is in a range from −2° C. to −10° C.

19. The method of claim 14, wherein the second duration of time is three to ten times longer in duration than the first duration of time.

20. The method of claim 19, wherein the second duration of time is less than 5 seconds.

21. The method of claim 14, wherein the second duration of time is a predetermined amount of time after an initiation of skin freezing.

22. The method of claim 14, further comprising adjusting the cooling applicator toward a post-treatment temperature that is higher than the treatment temperature after the second duration of time and while the cooling applicator is positioned and maintained against the skin surface so as to thaw frozen skin tissue.

23. The method of claim 22, wherein a thermoelectric cooler is thermally coupled with the cooling applicator, and wherein adjusting the cooling applicator toward the post-treatment temperature comprises reversing a current through the thermoelectric cooler.

24. The method of claim 22, wherein the post-treatment temperature is above 0° C.

25. The method of claim 24, wherein the post treatment temperature is less than 10° C.

26. The method of claim 22, wherein the cooling applicator is maintained in contact with the skin at the post-treatment temperature until the frozen skin tissue thaws.

27. The method of claim 14, wherein the pre-treatment temperature is colder than the treatment temperature.

28. The method of claim 14, further comprising measuring a force between the cooling applicator and the skin of the patient with a contact sensor.

29. The method of claim 28, further comprising automatically adjusting the first duration of time or the second duration of time based on the force measured by the contact sensor.

30. The method of claim 28, further comprising starting the first duration of time based on skin contact as determined by the contact sensor.

31. The method of claim 28, further comprising returning the cooling applicator to the pre-treatment temperature when skin contact is not determined by the contact sensor.

32. A method of reducing melanin in a skin of a patient using a cooling applicator of a treatment device, the method comprising:
- pre-cooling the cooling applicator to a pre-treatment temperature of −10° C. to −20° C. prior to positioning cooling applicator in contact with the skin;
- after the cooling applicator has been positioned onto the skin, cooling the cooling applicator toward the pre-treatment temperature for a first duration of time to condition at least an epidermal skin tissue to freeze while minimizing supercooling;
- after the first duration of time and while the cooling applicator is placed against the skin, controllably adjusting the cooling applicator toward a treatment temperature of −2° C. to −12° C. for a second duration of time that is longer than the first duration of time to freeze at least the epidermal skin tissue to reduce melanin in the skin, wherein the second duration of time begins after termination of the first duration of time; and
- after the second duration of time and while the cooling applicator is placed against the skin, adjusting the cooling applicator toward a post-treatment temperature between 0° C. to 40° C.

33. The method of claim 32, wherein the second duration of time is three to ten times longer in duration than the first duration of time.

34. The method of claim 33, wherein the second duration of time is less than 5 seconds.

35. The method of claim 32, wherein the second duration of time is a predetermined amount of time after an initiation of skin freezing.

36. The method of claim 32, wherein a thermoelectric cooler is thermally coupled with the cooling applicator, and wherein adjusting the cooling applicator toward the post-treatment temperature comprises reversing a current through the thermoelectric cooler.

37. The method of claim 36, wherein the post treatment temperature is less than 10° C.

38. The method of claim 32, wherein the cooling applicator is maintained in contact with the skin at the post-treatment temperature until the frozen skin tissue thaws.

39. The method of claim 32, wherein the pre-treatment temperature is colder than the treatment temperature.

40. The method of claim 32, further comprising measuring a force between the cooling applicator and the skin of the patient with a contact sensor.

41. The method of claim 40, further comprising automatically adjusting the first duration of time or the second duration of time based on the force measured by the contact sensor.

42. The method of claim 40, further comprising starting the first duration of time based on skin contact as determined by the contact sensor.

43. The method of claim 40, further comprising returning the cooling applicator to the pre-treatment temperature when skin contact is not determined by the contact sensor.

* * * * *